United States Patent [19]
Ganem et al.

[11] Patent Number: 5,861,240
[45] Date of Patent: *Jan. 19, 1999

[54] ISOLATED HUMAN HERPESVIRUS TYPE 8 SEQUENCES AND USES THEREOF

[75] Inventors: Donald E. Ganem; Weidong Zhong, both of San Francisco, Calif.

[73] Assignee: The Regents of the University of California, Oakland, Calif.

[*] Notice: This patent issued on a continued prosecution application filed under 37 CFR 1.53(d), and is subject to the twenty year patent term provisions of 35 U.S.C. 154(a)(2).

[21] Appl. No.: 607,412

[22] Filed: Feb. 28, 1996

[51] Int. Cl.$^6$ .............................. C12Q 1/70; C07K 14/03; C07K 16/08; C12N 15/38

[52] U.S. Cl. ........................... 435/5; 435/69.1; 435/69.3; 435/7.1; 435/6; 530/300; 530/389.4; 536/23.72; 536/23.1; 536/24.3

[58] Field of Search ...................................... 435/69.3, 7.1, 435/69.1, 5, 6; 530/300, 388.1, 389.4; 536/23.72, 23.1, 24.3; 436/518

[56] References Cited

FOREIGN PATENT DOCUMENTS

WO 96/06159  2/1996  WIPO .
WO 96/15779  5/1996  WIPO .
WO 97/27208  7/1997  WIPO .

OTHER PUBLICATIONS

Muralidhar et al. J. of Virology, Jun. 1998, vol. 72, pp. 4980–4988.
Sun et al P.N.A.S.USA, 1996, vol. 93, pp. 11883–11888.
Ambroziak, J., (1995) "Herpes–Like Sequences in HIV–Infected and Uninfected Kaposi's Sarcoma Patients," *Science* 268:582–583.
Beral, V. et al. (1990) "Kaposi's sarcoma among persons with AIDS: a sexually transmitted infection?" *Lancet* 335:123–128.
Boshoff, C., et al., (1995) "Kaposi's–sarcoma–associated herpesvirus in HIV–negative Kaposi's sarcoma," *Lancet* 345:1043–1044.
Chang, Y., et al., (1994) "Identification of Herpesvirus–Like DNA Sequences in AIDS–Associated Kaposi's Sarcoma," *Science* 266:1865–1869.
DiMaio, D., (1991) "Transforming Activity of Bovine and Human Papillomaviruses in Cultured Cells," *Adv. Cancer Res.* 56:133–159.
Moore, P. and Chang, Y., (1995) "Detection of Herpesvirus–Like DNA Sequences in Kaposi's Sarcoma in Patients with and those without HIV Infection," *New Engl. J. Med.* 332:1181–1185.
Perlman, David, (1996) "Virus Implicated in Kaposi's," *San Francisco Chronicle,* Mar. 1, 1996, p. A4.
Petti, L., et al., (1991) "Activation of the platelet–derived growth factor receptor by the bovine papillomavirus E5 transforming protein," *Embo J.* 10:845–855.
Schalling, M. et al., (1995) "A role for a new herpes virus (DSHV) in different forms of Kapos's sarcoma," *Nature Medicine* 1(7): 707–723.
Su, I. J., et al., (1995) "Herpesvirus–like DNA sequence in Kaposi's sarcoma from AIDS and non–AIDS patients in Taiwan," *Lancet* 345:722–723.
Wang, D., et al., (1985) "An EBV Membrane Protein Expressed in Immortalized Lymphocytes Transforms Established Rodent Cells," *Cell* 43:831–840.
Whitby, D., et al., (1995) "Detection of Kaposi sarcoma associated herpesvirus in peripheral blood of HIV–infected individuals and progression to Kaposi's sarcoma," *Lancet* 346: 799–802.
Cesarman, E. et al., 1995, N.E.J.M. vol. 332, pp. 1186–1191.
Change, Y. et al., 1994, Science, vol. 266. pp. 1865–1869.
Boshoff, C. et al., 1995, Lancet, vol. 345. pp. 1043–1044.

*Primary Examiner*—Mary E. Mosher
*Assistant Examiner*—Ali R. Salimi
*Attorney, Agent, or Firm*—Karl Bozicevic; Bozicevic & Reed LLP

[57] ABSTRACT

Isolated human herpesvirus type 8 nucleic acid sequences expressed in latently infected human cells including primary Kaposi's sarcoma cells, primary pulmonary tumor cells, and a body cavity based lymphoma cell line are disclosed. Methods of detecting HHV-8 infection and methods of inhibiting expression of the nucleic acid sequences in vivo are also disclosed.

12 Claims, 4 Drawing Sheets

CTCCCTCCTCACTCCAATCCCAATGCATGGATAGAGGCTTAACGGTGTTTGTGGCAGTT
                          M  D  R  G  L  T  V  F  V  A  V 60
CATGTCCCGGATGTGTTACTAAATGGGTGGCGCTGGAGGCTTGGGGCGATACCACCACT
 H  V  P  D  V  L  L  N  G  W  R  W  R  L  G  A  I  P  P  L 119
CGTTTGTCTGTTGGCGATTGGTGTTGTCCCCCCGAGTGGCCAGCGTGGCCCCGTAGCAT
  V  C  L  L  A  I  G  V  V  P  P  S  G  Q  R  G  P  V  A 178
TCAGGACACGAGTTGCAACGGGCGCGCACTGAAGCTAGCGTGCCCTCCCAAAGAGTGTC
 F  R  T  R  V  A  T  G  A  H   (60 aa)    SEQ ID NO: 2

237
AGTAAAATAAAATACAAAAGCACAATCACGGTTGCACCAAGCACAACATTAAACACATA

296
CAATGCTGAAGAGCAGGCGTATCGAGGGCATACCCGTGGCTCATAACACAGTCACAGTT

355
CAGAAGGCCGGCACGCGGTGTCAACCAGGCCACCATTCCTCTCCGCATTAAAGCACTCG

414
GTGGGGGAGGGTGCCCTGGTTGACACAATGTGCCGCGCATCAACCAGCGCGACGGAAGT

473
TGGCCTCCAGCAAAGCACATTTTGCACGCAAATGGCGTCCGCTCTCCCAAACCACACGA

532
ATGGTACCATGGCAAAAAACACTCCCTCAGAATGTATTGACCTTGTTTGTTAATGAAAT

591
TGTGGCACTGACTTCGGCAGACGCCAAGTGGTGGATATAGAACCACCTTTCATGGCAGT

650
ACATTGCAGCGTGTGCCACATGTTCAAAAACAATAAACAGATTAAAAGAAAAAAAAAAA

709
AAAAAAAA     SEQ ID NO: 1

FIG. 2

```
                                          P1
    1                               32 ◄─────── 52
    ACTGGGACTGCCCAGTCACCTTGGCGCCGCTTCACCTATGGATTTTGTGCTCGCTGCTTG

62
    CCTTCTTGCCGCTTCTGGTTTTCATTGGTGCCGCCGATTGTGGGTTGATTGCGTCGCTTTT

123
    GGCAATATACCCATCCTGGCTTTCGGCTAGGTTTTCCGTCCTACTTTTCCCACATTGGCCT

184
    GAGAGCTGTAGTACAAAAAACACCGCGCGGTCTGGAGCTCTCCATAAGCCCGCAGAACAAA

245
    AGCTGCGATTTGCCCAAAAACCTTGCCATGGCAACTATACAGTCACCCCTTGCGGGTTATT

306
    GCATTGGATTCAATCTCCAGGCCAGTTGTAGCCCCCTTTTATGATATGCGAGGATACTTAA

367
    CGTGTCTGAATGTGGAATATAATGTGAAAGGAAAGCAGCGCCCACTGGTGTATCAGAACAG

428
    TGGTGCACTACCTATCTGCTCATTCGTTGTTTCGGTTCTGTGTTTGTCTGATTCTTAGATA

489
    GTGTTGAGGTAATTCTAGAAAGCGGATTGAGTGTAAATCGGGCCACTTTGCCCTAAATGTG

550
    ACAATCTGGATGTGTATCTTATTGGTGCGTTGTGAAGCATTTTAAAATGCGTTTTAGATTG

611
    TATCAGGCTAGTGCTGTAATGGTGTGTTTATTTTTCCAGTGTAAGCAAGTCGATTTGAATG

672
    ACATAGGCGACAAAGTGAGGTGGCATTTGTCAGAAGTTTCAAAGTCGTGTAAGAACATTGG

733
    ACTAAAGTGGTGTGCGGCAGCTGGGAGCGCTCTTTCAATGTTAATGTTTTAATGTGTATGT

794
    TGTGTTGGAAGTTCCAGGCTAATATTTGATGTTTTGCTAGGTTGACTAACGATGTTTTCTT

855
    GTAGGTGAAAGCGTTGTGTAACAATGATAACGGTGTTTTGGCTGGGTTTTTCCTTGTTCGC

916
    ACCGGACACCTCCAGTGACCAGACGGCAAGGTTTTTATCCCAGTGTATATTGGAAAAACAT

977
    GTTATACTTTTGACAATTTAACGTGCCTAGAGCTCAAATTAAACTAATACCATAACGTAAT

1038
    GCAACTTACAACATAAATAAAGGTCAATGTTTAATCCATAAAAAAAAAAAAAAAAAAAAA
```

FIG. 3                SEQ. ID No: 3

-210                                                        CArG Box
GAAAGTTTATTAATGTTCATCCGTATTGTGTATATGTAATTTGGTTT|CCATATTTGG|

-153                                    AP1
TAGGAGTATGGAGTTTTCTTATGGATTATTA|aGgGTCA|GCTTGAAGGATGATGTTAA

-96                        CArG Box        CAAT Box
TGACATAAAGGGGCGTGGCTT|CCAAAAATGG|GT|GGCTAAcCT|GTCCAAAATATGGA

-39       TATA Box              AP1              →T1.1
ACACTGGA|gATAAAA|GGGGCCAGCT|TGAGTCA|GTTTAGCACTGGGACTGCCCAGTCA
                                        +1

FIG. 4A                                        SEQ ID NO: 4

→T0.7
[CGGGAACCTGGTGCCCTCCTCCC]$_{n \geq 12}$ (CGGGAACCTGGTGCCCTCCTCCC)TCCTCAC....
                                              +1
SEQ ID NO: 5                              SEQ ID NO: 6

FIG. 4B

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
( A ) LENGTH: 716 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:1:

```
CTCCCTCCTC ACTCCAATCC CAATGCATGG ATAGAGGCTT AACGGTGTTT GTGGCAGTTC    60
ATGTCCCGGA TGTGTTACTA AATGGGTGGC GCTGGAGGCT TGGGGCGATA CCACCACTCG   120
TTTGTCTGTT GGCGATTGGT GTTGTCCCCC CGAGTGGCCA GCGTGGCCCC GTAGCATTCA   180
GGACACGAGT TGCAACGGGC GCGCACTGAA GCTAGCGTGC CCTCCCAAAG AGTGTCAGTA   240
AAATAAAATA CAAAAGCACA ATCACGGTTG CACCAAGCAC AACATTAAAC ACATACAATG   300
CTGAAGAGCA GGCGTATCGA GGGCATACCC GTGGCTCATA ACACAGTCAC AGTTCAGAAG   360
GCCGGCACGC GGTGTCAACC AGGCCACCAT TCCTCTCCGC ATTAAAGCAC TCGGTGGGGG   420
AGGGTGCCCT GGTTGACACA ATGTGCCGCG CATCAACCAG CGCGACGGAA GTTGGCCTCC   480
AGCAAAGCAC ATTTTGCACG CAAATGGCGT CCGCTCTCCC AAACCACACG AATGGTACCA   540
TGGCAAAAAA CACTCCCTCA GAATGTATTG ACCTTGTTTG TTAATGAAAT TGTGGCACTG   600
ACTTCGGCAG ACGCCAAGTG GTGGATATAG AACCACCTTT CATGGCAGTA CATTGCAGCG   660
```

```
TGTGCCACAT GTTCAAAAAC AATAAACAGA TTAAAAGAAA AAAAAAAAA AAAAAA                716
```

(2) INFORMATION FOR SEQ ID NO:2:

(i) SEQUENCE CHARACTERISTICS:
        (A) LENGTH: 60 amino acids
        (B) TYPE: amino acid
        (C) STRANDEDNESS: single
        (D) TOPOLOGY: linear     (ii) MOLECULE TYPE: peptide     (v) FRAGMENT TYPE: N-terminal     (xi) SEQUENCE DESCRIPTION: SEQ ID NO:2:

```
Met Asp Arg Gly Leu Thr Val Phe Val Ala Val His Val Pro Asp Val
1               5                   10                  15

Leu Leu Asn Gly Trp Arg Trp Arg Leu Gly Ala Ile Pro Pro Leu Val
            20                  25                  30

Cys Leu Leu Ala Ile Gly Val Val Pro Pro Ser Gly Gln Arg Gly Pro
        35                  40                  45

Val Ala Phe Arg Thr Arg Val Ala Thr Gly Ala His
    50                  55                  60
```

(2) INFORMATION FOR SEQ ID NO:3:

(i) SEQUENCE CHARACTERISTICS:
        (A) LENGTH: 1096 base pairs
        (B) TYPE: nucleic acid
        (C) STRANDEDNESS: single
        (D) TOPOLOGY: linear     (ii) MOLECULE TYPE: cDNA     (xi) SEQUENCE DESCRIPTION: SEQ ID NO:3:

```
ACTGGGACTG CCCAGTCACC TTGGCTGCCG CTTCACCTAT GGATTTTGTG CTCGCTGCTT    60
GCCTTCTTGC CGCTTCTGGT TTTCATTGGT GCCGCCGATT GTGGGTTGAT TGCGTCGCTT    120
TTGGCAATAT ACCCATCCTG GCTTTCGGCT AGGTTTTCCG TCCTACTTTT CCCACATTGG    180
CCTGAGAGCT GTAGTACAAA AAACACCGCG CGGTCTGGAG CTCTCCATAA GCCCGCAGAA    240
CAAAAGCTGC GATTTGCCCA AAAACCTTGC CATGGCAACT ATACAGTCAC CCCTTGCGGG    300
TTATTGCATT GGATTCAATC TCCAGGCCAG TTGTAGCCCC CTTTTATGAT ATGCGAGGAT    360
ACTTAACGTG TCTGAATGTG GAATATAATG TGAAAGGAAA GCAGCGCCCA CTGGTGTATC    420
AGAACAGTGG TGCACTACCT ATCTGCTCAT TCGTTGTTTC GGTTCTGTGT TTGTCTGATT    480
CTTAGATAGT GTTGAGGTAA TTCTAGAAAG CGGATTGAGT GTAAATCGGG CCACTTTGCC    540
CTAAATGTGA CAATCTGGAT GTGTATCTTA TTGGTGCGTT GTGAAGCATT TTAAAATGCG    600
TTTTAGATTG TATCAGGCTA GTGCTGTAAT GGTGTGTTTA TTTTTCCAGT GTAAGCAAGT    660
CGATTTGAAT GACATAGGCG ACAAAGTGAG GTGGCATTTG TCAGAAGTTT CAAAGTCGTG    720
TAAGAACATT GGACTAAAGT GGTGTGCGGC AGCTGGGAGC GCTCTTTCAA TGTTAATGTT    780
TTAATGTGTA TGTTGTGTTG GAAGTTCCAG GCTAATATTT GATGTTTTGC TAGGTTGACT    840
AACGATGTTT TCTTGTAGGT GAAAGCGTTG TGTAACAATG ATAACGGTGT TTTGGCTGGG    900
TTTTTCCTTG TTCGCACCGG ACACCTCCAG TGACCAGACG GCAAGGTTTT TATCCCAGTG    960
TATATTGGAA AAACATGTTA TACTTTTGAC AATTTAACGT GCCTAGAGCT CAAATTAAAC    1020
TAATACCATA ACGTAATGCA ACTTACAACA TAAATAAAGG TCAATGTTTA ATCCATAAAA    1080
AAAAAAAAAA AAAAAA                                                    1096
```

( 2 ) INFORMATION FOR SEQ ID NO:4:

( i ) SEQUENCE CHARACTERISTICS:
( A ) LENGTH: 228 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:4:

| GAAAGTTTAT | TAATGTTCAT | CCGTATTGTG | TATATGTAAT | TTGGTTTCCA | TATTTGGTAG | 6 0 |
| GAGTATGGAG | TTTTCTTATG | GATTATTAAG | GGTCAGCTTG | AAGGATGATG | TTAATGACAT | 1 2 0 |
| AAAGGGGCGT | GGCTTCCAAA | AATGGGTGGC | TAACCTGTCC | AAAATATGGG | AACACTGGAG | 1 8 0 |
| ATAAAAGGGG | CCAGCTTGAG | TCAGTTTAGC | ACTGGGACTG | CCCAGTCA | | 2 2 8 |

( 2 ) INFORMATION FOR SEQ ID NO:5:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:5:

CGGGAACCTG GTGCCCTCCT CCC                                     2 3

( 2 ) INFORMATION FOR SEQ ID NO:6:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:6:

CGGGAACCTG GTGCCCTCCT CCCTCCTCAC                              3 0

ISOLATED HUMAN HERPESVIRUS TYPE 8 SEQUENCES AND USES THEREOF

FIELD OF THE INVENTION

The present invention relates to human herpesvirus type 8 nucleic acid sequences, polypeptides, antibodies, an assay device, methods of detecting the presence of HHV-8 in a human, and methods of inhibiting HHV-8 gene expression in a cell.

BACKGROUND OF THE INVENTION

Kaposi's sarcoma (KS) is the most common neoplasm occurring in patients with the acquired immunodeficiency syndrome (AIDS) (Beral, V. Cancer Surveys 10: 5–22 (1991)). The lesion is histologically complex, containing proliferating spindle-shaped cells thought to be of endothelial origin, as well as infiltrating mononuclear cells, plasma cells and abundant slit-like neovascular spaces. Although HIV infection is a major risk factor for KS development, epidemiologic studies suggest that it cannot be the sole determinant of KS risk, and that other cofactors, possibly sexually transmitted, play an important role in the etiology of the tumor (Beral, V. et al. (1990) Lancet 335:123–128). For example, HIV-positive male homosexuals are at least 20-fold more likely to develop KS than HIV-infected children or hemophiliacs. In addition, KS occurs in several clinical settings in the absence of HIV infection (Beral, V. (1991) Cancer Surveys 10:5–22). These and other observations have prompted a search for other viral agents that might be implicated in KS pathogenesis. Recently, DNA sequences of a novel member of the herpesvirus family, termed Kaposi's sarcoma-associated herpesvirus (KSHV) or human herpesvirus 8 (HHV-8), have been regularly identified in KS tumors from both HIV-positive (Chang, Y. et al. Science (1994) 266: 1865–1869; Ambroziak, J. (1995) Science 268:582–583; Su, I. J. et al. (1995) Lancet 345:722–723) and HIV-negative (Moore, P. and Chang, Y. (1995) New Engl. J. Med. 332:1181–1185; Schalling, M. et. al. (1995) Nature Medicine 1:707–708; Boshoff, C. et. al. (1995) Lancet 345:1043–1044) patients. This agent has been proposed as a candidate for the presumed etiologic co-factor in KS (Chang, Y. et al. Science (1994) 266: 1865–1869; Whitby, D. (1995) Lancet 346:799–802). Methods for convenient detection and control of this etiologic co-factor are currently unavailable clinically.

The references discussed herein are provided solely for their disclosure prior to the filing date of the present application. Nothing herein is to be construed as an admission that the inventors are not entitled to antedate such disclosure by virtue of prior invention.

SUMMARY OF THE INVENTION

Isolated human herpesvirus type 8 nucleic acid sequences expressed in latently infected human cells including primary Kaposi's sarcoma cells, primary pulmonary tumor cells, and a body cavity based lymphoma cell line are disclosed. Methods of detecting HHV-8 infection and methods of inhibiting expression of the nucleic acid sequences in vivo are also disclosed.

The nature of HHV-8 viral gene expression in KS tissue was examined revealing restricted viral gene expression in the tumor cells. Characterization of the major viral transcripts produced in infection shows them to be highly unusual RNAs quite distinct from those found in infection by related herpesviruses. These observations suggest that most infected cells in a KS lesion are latently infected, with lytic growth restricted to no more than a small subpopulation of cells. A role for antitumor chemotherapy is in the inhibition of expression of latently expressed transcripts.

Two small transcripts were identified and characterized, which transcripts represent the bulk of the virus-specific RNA transcribed from over 120 kb of the KSHV genome in infected cells. One is predicted to encode a small membrane protein; the other is an unusual polyadenylated RNA that accumulates in the nucleus to high copy number.

In one aspect, the invention provides a novel isolated DNA molecule encoding an HHV-8 gene product, which product is associated with the cell membrane of a cell having a latent infection of HHV-8. The cell may be any mammalian cell that can be infected by HHV-8 or any cell containing and expressing the isolated DNA molecule of the invention including, but not limited to, body cavity based lymphoma cells, cells from a Kaposi's sarcoma lesion, and cells from a primary pulmonary tumor. Preferably, the nucleic acid sequence of the isolated DNA molecule contains the DNA sequence designated herein as SEQ ID NO:1 or a portion thereof, which portion is at least 10 nucleotides in length.

Another aspect of the invention is an antisense RNA molecule of at least 10 nucleotides in length capable of hybridizing to sense transcript encoding the latently expressed HHV-8 cell membrane associated protein and having a sequence which is encoded by SEQ ID NO:1 or a portion thereof. In an embodiment of the invention in which the antisense nucleic acid is RNA thymine residues of SEQ ID NO:1 are replaced by uracil residues.

An embodiment of the invention is a cell containing the isolated DNA molecule encoding a latently expressed HHV-8 gene product, which product is localized to the cell membrane. Preferably the isolated DNA molecule is operably attached to exogenous transcription and translational control sequences in an expression cassette for expression in the cell.

Yet another aspect of the invention is a substantially pure polypeptide having an amino acid sequence (SEQ ID NO:2) deduced from SEQ ID NO:1. Also comprehended are polypeptide fragments duplicating only a part of the continuous amino acid sequence or secondary conformations within the HHV-8 latently expressed polypeptide predicted to be cell membrane associated.

In an embodiment of the invention, polypeptide analogs useful in the practice of this invention include those having one or more amino acid additions, substitutions, and/or deletions as compared to either naturally-derived or recombinant proteins, e.g., the latently produced HHV-8 cell membrane associated protein. Substitution analogs may be particularly useful in that such analogs may enable improved purification, stability or other useful features as compared to either naturally-derived or recombinant proteins.

Another aspect of the invention is an antibody that binds specifically to a polypeptide having an amino acid sequence of SEQ ID NO:2 or to an immunogenic epitope defined by a portion of SEQ ID NO:2.

Techniques for producing polyclonal and monoclonal antibodies for a compound are well known to those skilled in the art. Examples of references in which such techniques are described include Methods of Enzymology Volume 70 and Volume 73 Immunochemical Techniques parts A and B respectively Edited by Van Vunakis, H and Langone, J. L., Published by Academic Press 1980 (Part A) and 1981 (Part B), and Kohler, G. and Milstein, C, Nature, Vol. 265, p. 495 (1975).

Still another aspect of the invention is an isolated DNA molecule encoding an HHV-8 gene product, which product is localized to the nucleus of a cell latently infected with HHV-8. The cell may be any mammalian cell that can be infected by HHV-8 or any cell containing and expressing the isolated DNA molecule of the invention including, but not limited to, body cavity based lymphoma cells, cells from a Kaposi's sarcoma lesion, cells from a primary pulmonary tumor. Preferably, the nucleic acid sequence of the isolated DNA molecule contains the DNA sequence designated herein as SEQ ID NO:3 (FIG. 3) or a portion thereof, which portion is at least 10 nucleotides in length.

Still another aspect of the invention is an antisense nucleic acid molecule of at least 10 nucleotides in length capable of hybridizing to the sense transcript of HHV-8 localized to the nucleus and having a sequence SEQ ID NO:3 or a portion thereof. In an embodiment of the invention in which the antisense nucleic acid is RNA, thymine residues of SEQ ID NO:3 are replaced by uracil residues.

An embodiment of the invention is a cell containing the isolated DNA molecule encoding a latently expressed HHV-8 gene product, which product is localized to the cell nucleus. Preferably the isolated DNA molecule is operably attached to exogenous transcription and translational control sequences in an expression cassette for expression in the cell.

Another aspect of the invention is a method of detecting the presence of HHV-8 in a patient. The detection method of the invention includes the steps of contacting a biological sample from a patient suspected of being infected with HHV-8 with an antibody that binds specifically to an HHV-8 polypeptide gene product, which product is produced in a cell latently infected with HHV-8 and predicted to be localized to the cell membrane. Following the contacting step, binding of the antibody to an HHV-8 polypeptide of the biological sample is detected by standard immunochemical methods well known to one of ordinary skill in the art. The biological sample of the patient includes, but is not limited to, body fluids such as blood and serum, tissue samples, lysates of cells within a tissue sample, a histological preparation of a tissue, and the like.

An aspect of the invention is a method for detecting the presence of HHV-8 transcripts expressed in latently infected cells of a patient, which method includes the steps of detecting the presence of RNA produced during latent infection and localized to the cell nucleus, and encoded by DNA of SEQ ID NO:3 or a portion thereof.

A further aspect of the invention is a method for detecting the presence of HHV-8 transcripts expressed in latently infected cells of a patient, which method includes the steps of detecting the presence of mRNA complementary to the isolated DNA encoding an HHV-8 polypeptide produced during latent infection and localized to the cell membrane. In a preferred embodiment, the isolated DNA is detectable and has the sequence of SEQ ID NO:1 or a portion thereof.

Still another aspect of the invention is a method for inhibiting expression of HHV-8 DNA in a cell, which DNA encodes a polypeptide produced during latent infection and localized to the cell membrane, which method includes the steps of providing antisense RNA complementary to the mRNA encoding the polypeptide. The antisense RNA is at least 10 nucleotides in length and, when annealed to the mRNA, is capable of inhibiting translation of the mRNA into a functional HHV-8 polypeptide. The step of providing an antisense RNA is accomplished by introducing into the cell the antisense RNA or an isolated DNA molecule which, when transcribed within the cell, encodes the antisense RNA. The invention includes a method of antisense treatment comprising administering to a mammalian (human) cell in vitro or in vivo a pharmaceutical formulation comprising a pharmaceutically acceptable excipient carrier having dispersed therein a therapeutically effective amount of a compound of a nucleic acid capable of hybridizing to the sense RNA, which nucleic acid may be antisense RNA.

Another embodiment of the invention is a method for inhibiting expression of HHV-8 DNA in a cell, which DNA encodes an RNA produced during latent infection and localized to the cell nucleus. The method includes the steps of providing antisense RNA capable of hybridizing to the latently expressed HHV-8 sense RNA localized to the nucleus. The antisense RNA is at least 10 nucleotides in length and, when annealed to the sense RNA, is capable of inhibiting the function of the RNA. The step of providing an antisense RNA is accomplished by introducing into the cell the antisense RNA or an isolated DNA molecule which, when transcribed within the cell, encodes the antisense RNA.

As a feature of the invention, an immunoassay means may employ monoclonal or polyclonal antibodies. The immunoassay means may also include a solid or semi-solid support having sample-receiving areas. Exemplary sample-receiving supports include test tubes, microtiter plates, dipsticks, membranes, lateral flow devices, resins, PVC or latex beads, and nitrocellulose. The sample receiving areas of the support have surface-bound capture reagent (e.g. latently expressed HHV-8 cell membrane associated protein) capable of binding to a specific binding member (e.g., an antibody specific for the HHV-8 cell membrane associated protein). Surface-bound capture reagent may be HHV-8 cell membrane protein alone or may be a protein conjugate or other polymeric compound which is capable of presenting an epitope of the HHV-8 protein for binding by a specific binding member (e.g. specific antibody).

A detection means for monitoring the result of the immunoassay may be, for example, means to produce and/or measure a detectable reaction. Thus a detection means may comprise an enzyme and a substrate for the enzyme. Preferred detectable labels include enzymes (e.g. horse radish peroxidase, alkaline phosphatase), chemiluminescors (e.g. luciferin), and chromophores (e.g. dyes, colored latex beads, dyed particles, pigments, metal sol particles (e.g. gold or silver metal sol particles), dye encapsulated liposomes, carbon). The detectable label may be attached to the HHV-8 protein, the anti-HHV-8 protein antibody, or a second antibody directed against the anti-HHV-8 protein antibody. Examples of substrates for the detection of the label include o-phenylenediamine dihydrochloride; Amerlite Signal Reagent (available from Amersham International PLC); p-nitrophenol phosphate; and luciferase. It will be appreciated that an external detection device such as a spectrophotometer, liminometer or fluorimeter may be employed.

Still another embodiment of the invention is a histological method of detecting the presence of an HHV-8 polypeptide produced in cells latently infected with HHV-8, and which polypeptide is predicted to be associated with the membrane of the infected cell. According to the method of the invention, a tissue specimen of a patient suspected of being infected with HHV-8 is prepared for analysis by standard histological techniques well known to those of ordinary skill in the art. The histological sample is then contacted with an antibody that binds specifically to the HHV-8 polypeptide of the invention. The HHV-8 polypeptide-antibody complex is then detected by standard immunochemical techniques such as radioimmunolabelling or immunofluorescence.

An aspect of the invention is an assay device for detecting the presence of a latently expressed HHV-8 polypeptide in a biological sample of a patient. The assay device includes a solid support surface, such as a microtiter well, beads, and the like, to which is attached an antibody that binds specifically to the latently expressed HHV-8 polypeptide or an immunogenic epitope of the polypeptide. Binding of the HHV-8 polypeptide to the antibody is detected by standard immunochemical techniques well known in the art. Preferably the HHV-8 polypeptide is encoded SEQ ID NO:2 or a portion thereof. Attachment of the antibody to the solid support surface is covalent or non-covalent, performed by standard techniques well known in the art of immunochemical assay.

Another aspect of the invention is an assay device for detecting the presence of an antibody in a biological sample of a patient. The assay device includes a solid support surface, such as a microtiter well, beads, and the like, to which is attached an HHV-8 polypeptide or immunogenic epitope of the polypeptide that binds specifically to an antibody specific for the HHV-8 polypeptide. Binding of the HHV-8 polypeptide to the antibody in the biological sample is detected by standard immunochemical techniques well known in the art. Preferably the HHV-8 polypeptide is encoded SEQ ID NO:2 or a portion thereof. Attachment of the polypeptide or epitope to the solid support surface is covalent or non-covalent, performed by standard techniques well known in the art of immunochemical assay.

An embodiment of the invention features a kit for qualitatively or quantitatively detecting 1) a latently expressed HHV-8 cell membrane associated protein and/or 2) an antibody to the protein. The kit includes a means, such as an assay device of the invention, for detecting the protein or antibody by immunochemical techniques described above and well known in the art.

Alternatively, the kit may include a container containing a latently expressed HHV-8 cell membrane associated protein-specific antibody and a means for concentrating (e.g. immunoprecipitating) antibody-HHV-8 protein complexes formed by contacting a biological sample with the anti-protein antibody. It is understood that the alternative reaction of detecting an anti-HHV-8 cell membrane associated protein-specific antibody in a body fluid is also within the scope of the invention.

The kits described above may also include a means for comparing the result of the detection assay with that expected from a genuine product may comprise instructions describing the result expected of a genuine product (comprising, for example, a colour chart, calibration table or calibration curve), or it may comprise a sample of marked material identical to marked genuine product (to be analyzed alongside the unknown sample).

By "gene product" is meant the product of procaryotic or eucaryotic host expression (e.g., by bacterial, yeast, higher plant, insect and mammalian cells in culture) of host DNA sequences. By "recombinant gene product" is meant a product expressed by exogenous DNA sequences, which sequences are obtained by genomic or cDNA cloning or by gene synthesis. The products of expression in typical yeast (e.g., *Saccharomyces cerevisiae*) or procaryote (e.g., *E. coli*) host cells are free of association with any mammalian proteins. The products of expression in vertebrate {e.g., non-human mammalian (e.g., COS or CHO) and avian} cells are free of association with any human proteins.

The term "epitope" shall mean a sequence of five or more amino acids connected in a linear fashion which amino acids, by themselves or as part of a larger sequence, bind to an antibody generated in response to such sequence.

The term "expression cassette" refers to a DNA sequence which contains a coding region operably linked to suitable control sequences capable of effecting expression of the coding region in a compatible host. Expression systems invariably comprise a promoter, but, depending on the host intended, may contain additional critical DNA such as ribosome binding site or CAP site, termination sequence, and optional enhancer sequences upstream from the promoter or in other operable locations. The recombinant expression cassettes of the invention herein comprise a DNA of the invention encoding a latently expressed HHV-8 sequence operably linked to additional DNA sequences which are capable of effecting its expression. The expression cassette may reside on a transfer vector such as a plasmid or other vector which is self-replicating independently of the chromosome of the host cell, or may be constructed so that when inserted into a host cell it is able to integrate into the chromosome.

The term "promoter" shall mean a nucleotide sequence that, when operably linked to a DNA sequence of interest, promotes transcription of that DNA sequence.

By "substantially inhibit" or "substantial reduction" is meant a decrease or reduction in expression, transcription, translation, or a measurable phenotypic characteristic that is approximately 80% of the wild type level, preferably reduced to approximately 50% of the wild type level, or more preferably reduced to approximately 10% or less of the wild type level.

By "nucleotide sequence" is meant a sequence of deoxyribonucleotides or ribonucleotides in the form of a separate fragment or as a component of a larger construct. DNA encoding portions or all of the polypeptide of the invention can be assembled from cDNA fragments or from oligonucleotides that provide a synthetic gene which can be expressed in a recombinant transcriptional unit. Nucleotide sequences of the invention include DNA, RNA, and cDNA sequences, and can be derived from natural sources or synthetic sequences synthesized by methods known to the art.

By the term "isolated" nucleotide sequence is meant a nucleotide sequence that is not immediately contiguous (i.e., covalently linked) with either of the coding sequences with which it is immediately contiguous (i.e., one at the 5' end and one at the 3' end) in the naturally-occurring genome of the organism from which the nucleotide sequence is derived. The term therefore includes, for example, a recombinant nucleotide sequence which is incorporated into a vector, into an autonomously replicating plasmid or virus, or into the genomic DNA or a prokaryote or eukaryote, or which exists as a separate molecule independent of other sequences. It also includes a recombinant DNA which is part of a hybrid gene encoding additional polypeptide sequences.

By "substantially pure" is meant a compound such as a latently expressed HHV-8 cell membrane associated polypeptide, which is substantially free of other proteins, lipids, carbohydrates, or other materials with which it is naturally associated. A substantially pure HHV-8 polypeptide or epitope of the invention is at least 60%, by weight, free of other components, more preferably at least 75%, even more preferably at least 90%, and most preferably at least 99%, by weight, latently expressed HHV-8 cell membrane associated polypeptide. One skilled in the art can purify the HHV-8 polypeptide using standard techniques for protein purification, for example, by extraction from a natural source; by expression of a recombinant nucleic acid encoding a latently expressed HHV-8 cell membrane associated polypeptide or by chemically synthesizing the polypeptide. The purity of the HHV-8 polypeptide or epitope of the invention can be determined by any appropriate method, e.g., column chromatography, polyacrylamide gel electrophoresis, HPLC analysis, and/or amino-terminal amino acid sequence analysis.

These and other objects, advantages and features of the present invention will become apparent to those persons skilled in the art upon reading the details of the compositions, composition components, methods and method steps of the invention as set forth below.

It must be noted that as used in this specification and the appended claims, the singular forms "a", "an" and "the" include plural referents unless the context clearly dictates otherwise. Thus, for example, reference to "a DNA sequence" includes a plurality of DNA sequences and different types of DNA sequences.

Unless defined otherwise all technical and scientific terms used herein have the same meaning as commonly understood by one of ordinary skill in the art to which this invention belongs. Although any materials or methods similar or equivalent to those described herein can be used in the practice or testing of the present invention, the preferred methods and materials are now described. All publications mentioned herein are incorporated herein by reference for the purpose of describing and disclosing the particular information for which the publication was cited Before the methods and compositions of the present invention are described and disclosed it is to be understood that this invention is not limited to the particular methods and compositions described as such may, of course, vary. It is also to be understood that the terminology used herein is for the purpose of describing particular embodiments only, and is not intended to be limiting since the scope of the present invention will be limited only by the appended claims.

BRIEF DESCRIPTION OF THE DRAWINGS

FIG. 4 is a diagram of the nucleotide sequence (SEQ ID NO:4) upstream of the T1.1 transcript (FIG. 4A) and the nucleotide sequences (SEQ ID NO:5 and SEQ ID NO:6) upstream of the T0.7 transcript (FIG. 4B), including sequences functional in the expression of the transcript.

DESCRIPTION OF THE EMBODIMENTS

Example 1: General Procedures
Cell line and tumor specimen
The body cavity lymphoma cell line BCBL-1 (ATCC CRL 11982; U.S. application Ser. No. 08/529,881, herein incorporated by reference) was cultured in RPMI 1640 supplemented 10% in fetal calf serum (FCS).

The KS tumor was obtained from an AIDS associated pulmonary KS lesion.

The cutaneous KS tumor was obtained from an AIDS associated KS skin lesion.

It is included within the scope of the invention that any cell containing HHV-8 DNA may be used to obtain HHV-8 genomic sequences for the purpose of preparing cloned sequences for screening HHV-8 transcripts or cDNAs.

Figure 1:
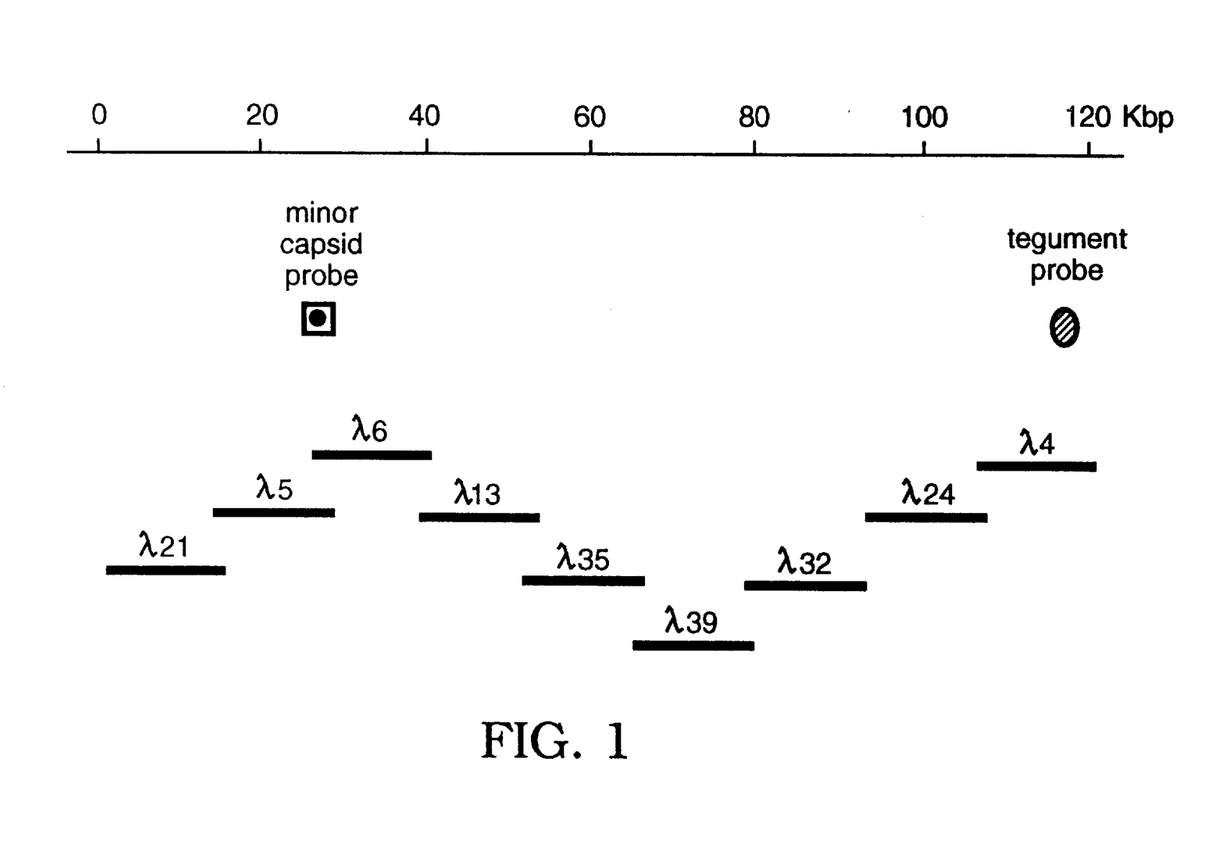
FIG. 1 is a diagram illustrating the cloning of KSHV (HHV-8) genomic fragments and identification of regions which are actively transcribed in a KS lesion. Overlapping clones of KSHV DNA (approximately 120 kbp) isolated from a bacteriophage lambda library of KS genomic DNA are shown.
Figure 2:
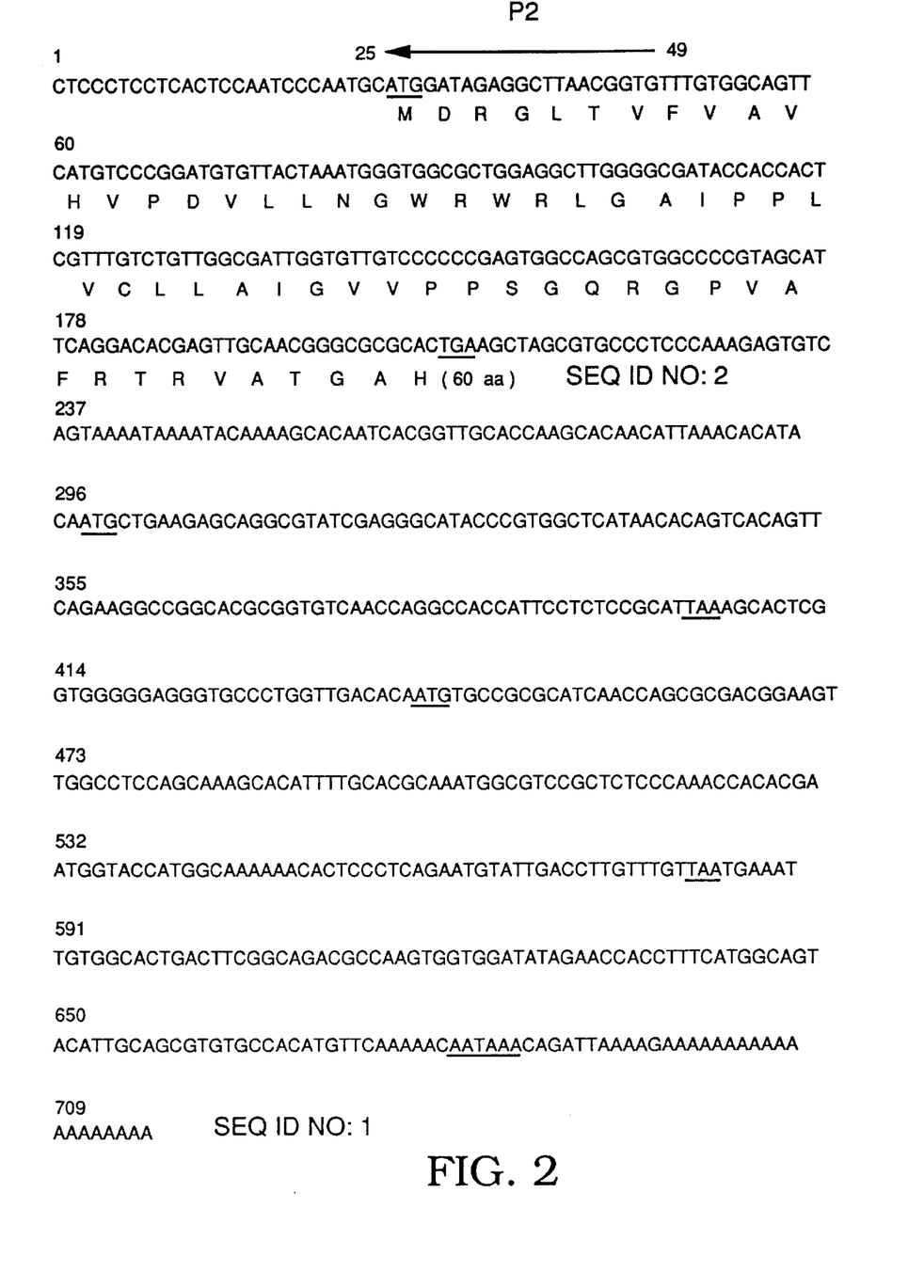
FIG. 2 is the DNA sequence of the isolated nucleic acid molecule (SEQ ID NO:1) encoding the latently expressed RNA and a polypeptide having a deduced amino acid sequence designated SEQ ID NO:2 and predicted to be a membrane associated polypeptide in cells in which it is expressed.
Figure 3:
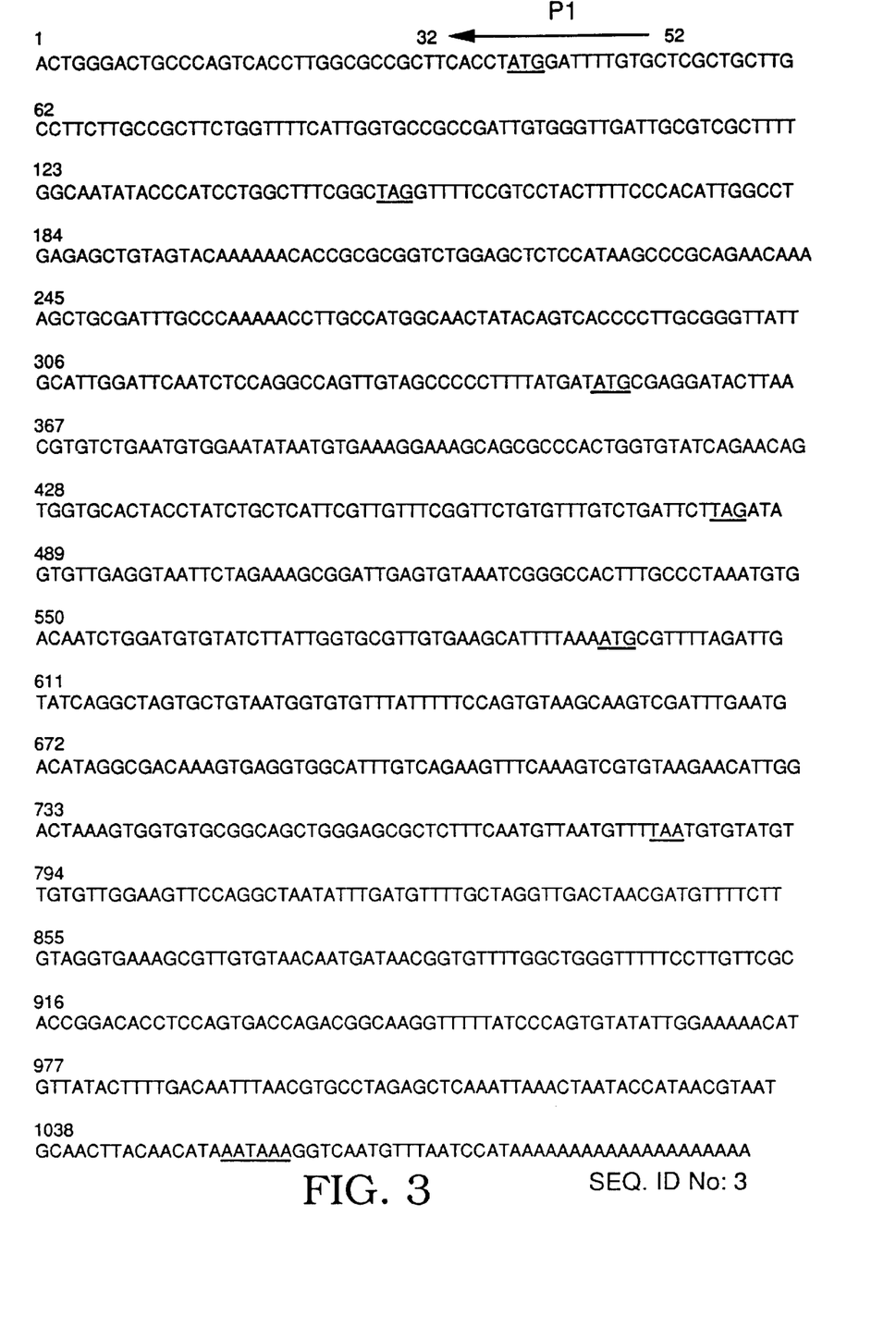
FIG. 3 is the DNA sequence of the isolated nucleic acid molecule (SEQ ID NO:3) encoding latently expressed RNA localized to the nucleus of a cell expressing the DNA.

RNA and cDNA probe preparation. Total RNA was extracted by the RNAzol method (Tel-Test, Inc) according to the manufacturer's directions; hybridization probes were prepared by randomly-primed DNA synthesis using synthetic hexanucleotides (Amersham) as described by the manufacturer.

cDNA library screening. An oligo-dT primed cDNA library from poly(A)+RNA of a cutaneous KS lesion was constructed in this laboratory using the Lambda ZAP-cDNA Synthesis Kit (Stratagene) according to the manufacturer's protocol. Two probes, 21-0.8 K and 4-1.6 K obtained by labeling DNA from the HHV-8 genomic clones number 21 and 4 were used to screen the cDNA library. The sequences shown in FIG. 2 and FIG. 3 represent the longest cDNA isolates. The DNA sequences of these two cDNA clones are identical to the sequences of corresponding genomic regions of HHV-8 which were cloned from the pulmonary KS specimen (FIG. 1).

Primer extension. Primer extension reactions were performed as follows: 5 $\mu$g of total KS RNA and 1 pmol of end-labeled oligonucleotide primer were mixed in 10 $\mu$l of annealing buffer (100 mM NaCl, 20 mM Tris pH 8.3, 0.1 mM EDTA, 5 units/$\mu$l RNasin), heated at 90° C. for 3 min., 56° C. for 20 min., and then slowly cooled to room temperature. Forty $\mu$l of extension mixture containing 62.5 mM Tris pH 8.3, 94 mM KCl, 3.75 mM $MgCl_2$, 12.5 mM DTT, 1.25 mM each of dATP, dCTP, dGTP and dTTP, 0.6 $\mu$g actinomycin D, 30 units RNasin, and 400 units of Super-Script II reverse transcriptase (GIBCO) was added to the RNA mixture. After incubation for 60 min at 42° C., the reaction was stopped by extraction with phenol and chloroform. Extension products were precipitated with ethanol, resuspended in sample buffer, then resolved on a 6% acrylamide sequencing gel and autoradiographed.

Primer extension assay to map the 5' end of a transcript. To prepare the cDNA probe used in primer extension reactions, about 100 ng of Poly(A)+RNA extracted from the pulmonary KS tumor was reverse transcribed in a standard reaction containing 0.5 mM of dATP, dGTP and dTTP, 0.1 mM dCTP, 50 $\mu$Ci [1 Ci=37 GBq] a-$^{32}$P-dCTP, 50 units of RNasin ribonuclease inhibitor (Promega), 1× concentration of hexanucleotide mixture (Boehringer Mannheim) and 200 units of M-MLV reverse transcriptase in a total volume of 50 ml. The reaction was carried out at 37° C. for 1 hour and stopped by heating at 95° C. for 5 min. The labeled cDNA probe was added to the KSHV filter prehybridized in Church hybridization solution (Church, G. M. and Gilbert, W. (1984) Proc Nat Acad Sci USA 81:1991–1995) and incubated overnight at 65° C.; the filter was then washed in 40 mM $NaHPO_4$, 0,1% SDS, 1 mM EDTA, pH 8.0 and subjected to autoradiography.

Example 2: Preparation of Genomic Clones for Use in Screening for HHV-8 Expression Identification of expressed viral genes. HHV-8 DNA sequences were first identified by Chang (Chang, Y. et al. Science (1994) 266: 1865–1869) using PCR-based representational difference analysis as DNA present in KS but not uninvolved tissue samples from an AIDS-related KS case. This yielded two short (330 and 631 bp) DNA fragments with homology to herpesviral capsid and tegument components, respectively (Chang, Y. et al. (1994) supra). From the sequence of these clones oligonucleotide primers were designed herein that allowed amplification and cloning of the corresponding regions from genomic DNA extracted from a fatal case of AIDS-associated pulmonary KS. To obtain more extensive clones of HHV-8 DNA, a library of KS genomic DNA (from the same pulmonary KS tumor) was made in bacteriophage lambda.

Genomic DNA was extracted from an AIDS-associated pulmonary KS lesion using previously described methods (Hansen, L. J., (1993) Molec. Cell. Biol. 13:659–667), and was partially digested with Sau3AI. Restriction fragments from 10 to 20 kb were gel-purified and cloned into the bacteriophage vector Lambda FIX II (Stratagene). The initial probes used to screen the library derived from two published sequences, one of which (approximately 900 bp) corresponds to the KSHV minor capsid gene and the other (about 630 bp) to a KSHV tegument gene (Chang, Y. et al. Science (1994) 266: 1865–1869). Each probe was prepared herein from the same pulmonary KS tumor by PCR amplification followed by plasmid subcloning. Chromosome walking was performed herein by isolating additional 1–3 kb subclones from the termini of each newly isolated phage insert, labeling them by random priming using synthetic hexanucleotide primers (RediPrime DNA Labeling System, Amersham) and $^{32}$P-dCTP, and applying each labeled probe so prepared to the original KS genomic library.

The library was initially screened with the capsid- and tegument-specific probes described above (Chang, Y. (1994), supra), and a series of overlapping clones was then isolated using the probes prepared herein, which clones span approximately 120 kb of the genome (FIG. 1).

It is within the scope of the invention that HHV-8 genomic clones may be prepared from any cell containing HHV-8 genomic sequences by one of ordinary skill in the art by the method described and guidance provided herein. Alternatively, the HHV-8 genomic DNA may be obtained from a cell line capable of expressing HHV-8 viral particles (ATCC CRL 11982; U.S. application Ser. No. 08/529,881). The HHV-8 genomic clones may be obtained by standard techniques of isolating the viral particles from the cell, isolating the viral DNA from the particle, and subcloning the viral DNA to produce overlapping clones spanning the viral genome.

Example 3: HHV-8 Gene Expression in Primary KS Cells

HHV-8 gene expression in primary KS cells was determined by the following procedures. DNA from each of the HHV-8 genomic clones was digested with SalI or SacI, electrophoresed through 0.8% agarose and stained with ethidium bromide. These two restriction enzymes were chosen because they cleave on either side of the insert but not in the phage arms, and generate a suitable number of HHV-8-specific fragments. These DNA fragments were transferred to a nylon filter, then hybridized with a radiolabelled cDNA probe representative of transcripts present in KS. This probe was prepared by reverse transcribing polyA+ RNA from the same KS tumor from which the HHV-8 genomic clones were prepared, using random oligonucleotide primers and MuLV reverse transcriptase. The probe thus represents all cellular as well as viral transcripts. As a control for the sensitivity of the method, transcripts of a single-copy, cellular housekeeping gene, GAPDH, could be readily detected.

When the KS pulmonary tumor cDNA was hybridized to the filter-bound HHV-8 genomic DNA clones, a strikingly simple pattern was observed. The majority of the cloned HHV-8 fragments annealed poorly or not at all to the probe, with detectable hybridization limited primarily to clones designated numbers 4, 24 and 21. Subsequent experiments using plasmid subclones of these phage revealed that: (i) the hybridization to clones 4 and 24 mapped to a 1.6 kb restriction fragment in their overlapping region; and (ii) the hybridization to clone 21 was primarily to a 0.8 kb subfragment. To more directly visualize the transcripts corresponding to these genomic regions, radiolabeled probes were prepared from these 1.6 and 0.8 kb HHV-8-specific subclones and annealed to Northern blots of total RNA from the pulmonary KS tumor. This showed that the RNA annealing to clone 21 corresponded to a 1.1 kb transcript (transcript designated T1.1), while that corresponding to clones 4 and 24 was a 0.7 kb RNA (transcript designated T0.7). Neither transcript was detectable in normal lung tissue from the same patient, and hybridization to GAPDH probe confirmed that equal amounts of KS and non-KS RNA were loaded in each lane. The same transcriptional pattern seen here was also seen in a second KS tumor by Northern blotting. In addition, cDNA cloning from a third KS tumor also revealed the expression of these same two transcripts in that tumor. This indicates that this pattern is highly representative of gene expression in AIDS-associated KS.

Example 4: HHV-8 Gene Expression in BCBL-1 cells

Characterization of HHV-8 viral gene expression in latent BCBL-1 infected with HHV-8. BCBL-1 cells (ATCC CRL 11982; U.S. application Ser. No. 08/529,881) were seeded in two flasks at a density of $2\times10^5$ cells/ml in fresh RPMI 1640 medium containing 10% FCS. TPA was added to one flask to a concentration of 20 ng/ml and treated and untreated cells were incubated for 48 hours at 37 C. and 5% $CO_2$. Total RNA was extracted using RNazol (Tel-Test, Inc., Friendswood, Tex.) according to the protocol of the supplier, and polyA+ RNA selected utilizing the Oligotex mRNA Kit (Quiagen). To generate radiolabeled cDNA probes, 100 ng of poly A+ RNA from TPA-treated and untreated BCBL-1 cells were reverse transcribed using 200 units Mo-MuLV reverse transcriptase in a total volume of 50 $\mu$l containing 0.5 mM dATP, dGTP dTTP, 0.1 mM dCTP, 50 $\mu$Ci [1 Ci=37 gBq] alpha-$^{32}$P-dCTP, 50 units RNasin (Promega) and ca. 50 pmol. random hexanucleotide primers (Boehringer, Mannheim). The reaction mixture was incubated at 37° C. for 1 hour and was stopped by heating to 95° C. for 5 min. The labelled cDNA probes were hybridized to filters containing cloned HHV-8 DNA at 65° C. overnight in Church hybridization buffer (Church, G. M. and Gilbert, W. (1984) Proc Nat Acad Sci USA 81:1991–1995). To produce filters, 9 lambda clones containing approx. 120 kbp of KSHV DNA were digested with SalI or SacI and 2 to 4 $\mu$g of each clone was loaded on a 0.8% agarose gel, electrophoresed and transferred to nylon filters (Hybond-N).

Examination of the pattern of HHV-8 expression in the BCBL-1 line has the advantage that EBV is absent from these cells (see application Ser. No. 08/529,881). DNA from HHV-8 genomic clones was digested with Sal I or Sac I and the resulting fragments separated on an agarose gel, stained with EtBr and transferred to a nylon filter; the complex array of fragments on this filter subsumes approximately 120 kb of the viral genome.

To identify which regions of this DNA are actively transcribed, we prepared polyA+ RNA from BCBL-1 cells and used it as a template for the production of radiolabeled cDNA, using random primers and MuLV reverse transcriptase. This probe should represent both viral and cellular transcripts; to identify the transcribed viral genes this probe was annealed to the panel of filter-bound, cloned genomic HHV-8 DNAs just described.

Only a small subset of HHV-8 DNA fragments were detected in this assay. This signal was the result of the expression of two RNAs (of 1.1 and 0.7 kb) demonstrating a dramatic restriction of viral gene expression that is highly suggestive of latent infection (Roizman, B. "Herpesviridae: a brief introduction", in B. N. Fields (ed) Virology (2nd edition; New York: Raven Press, 1990) pp. 1787–1793; Kieff, E. "Epstein-Barr virus and its replication", in B. N. Fields (ed) Virology (2nd edition; New York: Raven Press, 1990) pp. 1902–1903).

Thus, under normal growth conditions, BCBL-1 cells (ATCC CRL 11982) display a highly restricted pattern of gene expression. However, upon treatment with the phorbol ester TPA, lytic viral replication is induced, as judged by the induction of viral DNA synthesis, transcription of extensive regions of the viral genome and the accumulation of enveloped virions in the cells and medium (see application Ser. No. 08/529,881). This indicates that the restricted pattern of gene expression seen in the absence of TPA corresponds to an authentic latent infection. The patterns of expression in KS tumors and in uninduced BCBL cells are strikingly similar, with the principal signals in both cases emanating from lambda clones 4, 21 and 24. These findings strongly support the notion that most infected cells in KS are latently infected.

It is unlikely that the two RNAs identified thus far are the sole viral transcripts present in KS, for several reasons. First, the library of cloned fragments screened in FIG. 1 does not include the complete viral genome, raising the possibility that additional transcripts may be encoded by regions not yet cloned. Second, the screening method used herein (FIG. 1) is potentially biased in favor of abundantly expressed RNAs, so that low-level transcripts may have passed undetected. However, the data clearly establish that HHV-8 infection of cells in KS involves a dramatic restriction of viral gene expression indicating that most infected cells in KS are not productively infected.

Characterization of viral gene expression during induced lytic program in BCBL-1 cells. Strong evidence that the above results represent a true latent infection rather than an aberrant or "dead end" infection could be supplied by demonstrating that, in response to the appropriate stimuli, a switch to productive (lytic) replication is induced. In EBV latency in B cells, many stimuli have been shown to induce lytic replication and virion production. Accordingly, HHV-8 replication may be induced by treatment of BCBL-1 cells with a variety of chemical and biological agents including phorbol esters, butyrate, surface Ig crosslinking, 5-azacytidine and deregulated expression of the EBV BZLF1 transactivator (zur Hausen, H. et al. (1979) Nature 272:373–375; Luka, J. (1979) Virology 94:228–231; Takada, K. (1984) Int. J. Cancer 33:27–32; Ben-Sasson, S. (1981) Int J. Cancer 28:131–135).

TPA is an authentic inducer of the lytic program in BCBL-1 cells (ATCC CRL 11982; application Ser. No. 08/529,881) indicating that DNA replication and late gene expression occur during TPA induction. When the phorbol ester TPA was added to the culture at 20 ng/ml, a dramatic inhibition of cellular growth was observed over the next 48 hours, with the appearance of considerable cytotoxicity. PolyA+ RNA was prepared from such cells and reverse-transcribed into radiolabeled cDNA as described above. When this probe was applied to the standard array of filter-bound restriction fragments of cloned HHV-8 DNA, virtually every HHV-8 fragment tested annealed to the probe, indicating widespread transcription of the viral genome.

Example 5: Characterization of Viral Transcripts Isolated from HHV-8 Infected KS Cells.

Latently expressed HHV-8 viral transcripts were obtained from cells of a cutaneous KS lesion from an AIDS patient different from the patient from whom the pulmonary KS tumor was obtained. To characterize in more detail the structure of the RNAs T1.1 and T0.7, an oligo dT-primed cDNA library prepared from a cutaneous KS lesion was probed with probes 21-0.8 K (a 0.8 kbp fragment from lambda clone 21) and 4-1.6 K (a 1.6 kbp fragment from lambda clone 4). The DNA sequences of the cDNA clones are shown in FIG. 2 for the 1.1 kb transcript and in FIG. 3 for the 0.7 kb transcript. Both sequences contained canonical polyadenylation signals (AAUAAA) 12–24 nt. upstream of a homopolymeric run of adenine residues. The sizes of the clones (1096 and 717 nt.) conformed closely to the approximate sizes of the transcripts estimated by Northern blotting, suggesting that the clones were full-length. To verify this, the 5' end of each RNA was mapped by primer extension, using the synthetic oligonucleotide primers indicated by overlining in FIG. 2 (primer P2) and FIG. 3 (primer P1). In addition, the position of the 5' end of T1.1 was independently confirmed by RNase protection experiments using RNA probes spanning the start site.

Figure 4A:
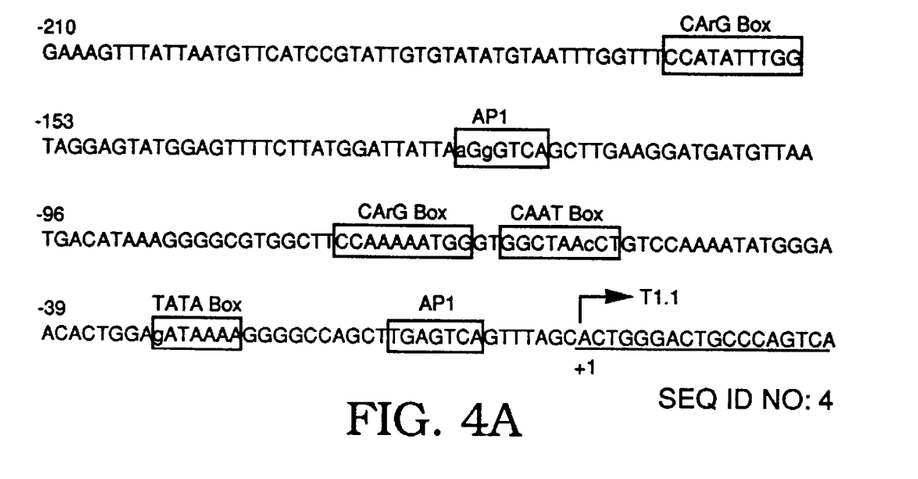
Figure 4B:
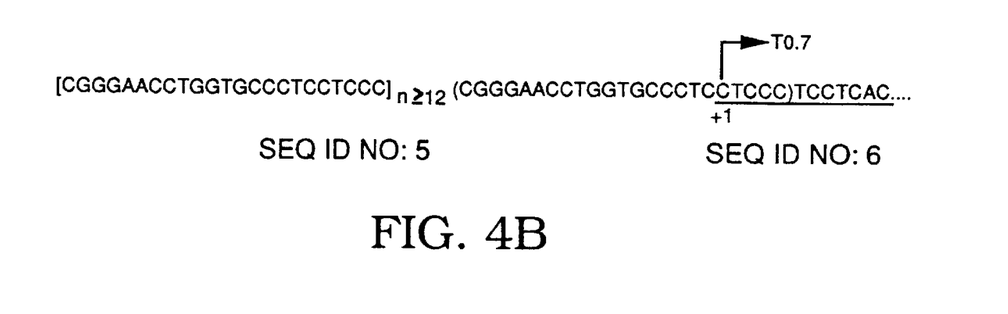

The nucleotide sequences of the genomic loci corresponding to these RNAs was determined and compared with their respective cDNA sequences. This revealed complete colinearity in the body of each transcript, indicating that (i) neither RNA is derived by splicing or RNA editing; and (ii) that the sequences encoding both transcripts are entirely conserved in two epidemiologically unrelated isolates of HHV-8. The HHV-8 genomic DNA sequence 5' to each start site is shown in FIG. 4A (for T1.1) and FIG. 4B (for T0.7). The putative regulatory sequences for T1.1 appear to conform to expectation for a typical pol II promoter: they include an appropriately positioned TATA element, a potential CAAT box and several potential AP1 sites. In addition, the sequence displays two so-called CArG (C A-rich G-containing) boxes, sequences that have been previously identified to control expression in muscle, including vascular smooth muscle (Miwa, T. and Kedes, L. (1987) Molec. Cell Biol. 7:2803–2813; Mohun, T. J. (1989) EMBO J. 8:1153–1161; Miwa, T. (1991) Molec. Cell Biol. 11:3296–3306). By contrast, the T0.7 upstream regulatory sequences are highly distinctive. No TATA box is present, and the start site is embedded within the distal region of the sequence CGGGACCTGGTGCCCTCCTCCC (SEQ ID NO:5), which is directly repeated over 12 times 5' to the start site. Since there was no evidence for RNA splicing in this region, it is likely that these sequences supply promoter function.

Cellular Localization of Transcript T1.1 to the Nucleus. Although T1.1 is translationally open from its start site, the first in-frame AUG is not reached until nucleotide 39, and this start codon is in a suboptimal sequence context for initiation. As a result, the 5' most open reading frame (orf) is only 37 aa long. Two other short orfs are also present on the RNA, though their internal position makes their translation quite problematic. These peculiarities suggested that this transcript might not serve as a mRNA in vivo. This inference is further supported by analysis of the subcellular localization of this RNA.

Examination by in situ hybridization of HHV-8 infected KS cells expressing T1.1 revealed the transcript to be localized primarily to the nucleus. To affirm this result biochemically, and to determine whether other viral gene products are important in the nuclear localization of this RNA. The subcellular distribution of T1.1 RNA in transfected cells expressing only this viral gene product was examined. 293T cells were transiently transfected with a genomic clone spanning the T1.1 locus (including the regulatory signals shown in FIG. 4A) and polyA+ RNA from nuclear and cytoplasmic fractions was examined by Northern blotting. T1.1 RNAs were localized primarily to the nucleus, under conditions in which GAPDH mRNA (control) was largely cytoplasmic. This indicates that information for nuclear localization is intrinsic to the transcript and that no other viral functions are required to assure its nuclear delivery or retention. Most likely, interactions with cellular factor(s) are required for nuclear localization In this connection, it is noteworthy that several lymphotropic herpesviruses are known to produce abundant nuclear RNAs. Cells latently infected by EBV produce the so-called EBER RNAs, small, structured, RNAs that associate in the nucleus with several host proteins, including the autoantigen La (Lerner, M. et al. (1981) Proc. Nat. Acad. Sci. USA 78:805–809). EBERs, however, are nonpolyadenylated and are transcribed by RNA polymerase III (Howe, J. G. and Shu, M. -D. (1993) Molec. Cell Biol. 13:2655–2665). Herpesvirus saimiri, a simian virus related to HHV-8, encodes several abundant U-like nuclear RNAs during latent infection. Like host U RNAs, these are complexed with cellular Sm proteins in RNP particles; although they are transcribed by RNA polymerase II, they are also nonpolyadenylated (Lee, S. et al. (1988) Cell 54:599–607). The accumulation of stable, nuclear polyA+ transcripts in KSHV/HHV-8 infection is unique among herpesviruses. Perhaps they too are organized into a snRNP-like particle with actions on RNA processing or transport. Alternatively, the naked RNA might play a structural role in the nucleus or have catalytic function; similar speculations have been proffered for the cellular RNA Xist, a large, noncoding, polyadenylated nuclear transcript implicated in X chromosome inactivation (Brockdorff, N. et al. (1992) Cell 71:515–526; and Brown, C. (1992) Cell 71:527–542). Another possibility is that these RNAs might be stored in the nucleus, awaiting transport to the cytosol under the influence of another viral gene product, e.g. one analogous to HIV rev. If so, however, such a product is not being expressed during latent infection of target cells in KS.

Characterization of Transcript T0.7 and It's Predicted Protein Product. The sequence of T0.7 displays only a short open reading frames (FIG. 3). Its longest coding region, only 60 amino acids, is positioned at the 5' end of the RNA, a position compatible with its translation by scanning ribosomes. In situ hybridization studies reveal that T0.7 RNAs do access the cytoplasmic compartment, consistent with their likely messenger function. The sequence of the 5' orf has no homologs in the GenBank data base; however, it displays a strikingly hydrophobic nature, strongly suggesting that its product is a membrane protein, most likely with at least two transmembrane domains. The small size and extreme hydrophobicity of this polypeptide recall similar attributes of the 44 amino acid E5 protein of bovine papilloma virus, a major transforming protein that acts via interaction with the PDGF receptor in cell membranes (DiMaio, D. (1991) Adv. Cancer Res. 56:133–159; Petti, L. et al. (1991) EMBO J. 10:845–855). Its expression during latency, its likely membrane association and its location downstream of genomic repeats also recall similar features of the major transforming protein of EBV, LMP-1 (latent membrane protein 1) (Wang, D. et al. (1985) Cell 43:831–840). However, the product of T0.7 has no homology to LMP-1 or to E5 at the primary sequence level.

Example 6: Detection of HHV-8 Infection in a Patient

Transcripts expressed by HHV-8 during latent infection may be detected by in situ hybridization or by Northern analysis. Cells of a patient suspected of having an HHV-8 infection are collected from the patient. Preferably the cells are from a tumor, a KS lesion, or other tissue suspected of being infected with HHV-8. mRNA is isolated from the cells of the patient by standard techniques as described herein and separated by gel electrophoresis. Tissue samples are prepared for in situ hybridization by standard techniques. The presence of an HHV-8 latently expressed transcript of the invention is detected by hybridization to a detectable nucleic acid probe having SEQ ID NO:1 or a portion thereof. Alternatively, the transcript is contacted with a detectable probe having SEQ ID NO:3 or a portion thereof.

The polypeptide gene product expressed during latent HHV-8 infection and associated with the cell membrane is detected by immunoassay in which an antibody specific for the polypeptide is used to bind to the polypeptide and detect the polypeptide in a biological sample of a patient suspected of having an HHV-8 infection.

The biological sample may be a tissue sample containing cells suspected of being infected with HHV-8 such as a tumor, a KS lesion, or other cells capable of being infected by HHV-8. The anti-HHV-8 cell membrane associated protein is preferably attached to a solid support such as a microtiter well, solid beads, and the like. Alternatively, a tissue sample is prepared by histological techniques. The anti-HHV-8 antibody is contacted with the intact HHV-8 infected cells or with a cell lysate from the biological sample of the patient. Detection of specific binding between the anti-HHV-8 antibody and the HHV-8 protein is performed by standard immunochemical techniques as described herein and which techniques are well known in the art.

A method of detecting antibody to latently expressed HHV-8 cell membrane associated protein in a biological sample of a patient is another aspect of the invention. The method involves providing an immobilized latently expressed HHV-8 cell membrane associated protein or an immunogenic epitope of the protein immobilized on a solid support surface. This is followed by contacting the protein with a biological sample from a patient, such as a blood, serum or other sample suspected of containing an antibody to the HHV-8 protein. Binding of the antibody to the HHV-8 protein is detected by standard immunoassay techniques well known in the art.

Example 7: Inhibition of HHV-8 Gene Expression in Latently Infected Cells

HHV-8 transcripts of latently infected cells are inhibited from functioning by annealing a complementary nucleic acid sequence thereby preventing translation or proper folding of the transcript.

According to the invention, transcript T0.7 is inhibited from being translated in a latently infected cell by providing a nucleic acid sequence of at least 10 nucleotides in length and complementary to T0.7, capable of annealing to T0.7, and preventing translation of the transcript into the latently expressed HHV-8 cell membrane associated polypeptide. The nucleic acid sequence provided preferably has the sequence of SEQ ID NO:1 or a portion thereof capable of substantially inhibiting translation of T0.7 sufficient to prevent production of the latently expressed HHV-8 cell membrane associated protein.

The antisense nucleic acid capable of annealing to T0.7 is provided to a latently infected cell by introducing into the infected cell a nucleic acid having the sequence of SEQ ID NO:1 or a portion thereof.

Alternatively, a DNA encoding an antisense nucleic acid capable of annealing to T0.7 is introduced by the above means of delivery, which DNA sequence is included in an expression cassette having sequences that allow recombination into the genome of the HHV-8 infected cell and allow expression of the antisense nucleic acid in the infected cell.

Transcript T1.1 which remains as an RNA molecule localized to the cellular membrane is inhibited from folding properly by providing a nucleic acid sequence of at least 10 nucleotides in length and complementary to T1.1, capable of annealing to T1.1, and preventing normal folding of the transcript. The nucleic acid sequence provided preferably has the sequence of SEQ ID NO:3 or a portion thereof capable of substantially inhibiting folding of T1.1 sufficient to prevent production of the latently expressed HHV-8 normally folded nuclear transcript.

The antisense nucleic acid capable of annealing to T1.1 is provided to a latently infected cell by introducing into the infected cell a nucleic acid having the sequence of SEQ ID NO:3 or a portion thereof.

Alternatively, a DNA encoding an antisense nucleic acid capable of annealing to T1.1 is introduced by the above means of delivery, which DNA sequence is included in an expression cassette having sequences that allow recombination into the genome of the HHV-8 infected cell and allow expression of the antisense nucleic acid in the infected cell.

Nucleotide sequences, including antisense sequences, can be therapeutically administered by various techniques known to those skilled in the art. Delivery of nucleotide sequences can be achieved using free polynucleotide or a recombinant expression vector such as a chimeric virus or a colloidal dispersion system. Especially preferred for therapeutic delivery of nucleotide sequences is the use of targeted liposomes.

Targeting of the therapeutic reagent to specific tissues is desirable to increase the efficiency of delivery. The targeting can be achieved by passive mechanisms via the route of administration. Active targeting to specific tissues can also be employed. The use of liposomes, colloidal suspensions, and viral vectors allows targeting to specific tissues by changing the composition of the formulation containing the therapeutic reagent, for example, by including molecules that act as receptors for components of the target tissues. Examples include sugars, glycolipids, polynucleotides, or proteins. These molecules can be included with the therapeutic reagent. Alternatively, these molecules can be included by indirect methods, for example, by inclusion of a polynucleotide that encodes the molecule, or by use of packaging systems that provide targeting molecules. Those skilled in the art will know, or will ascertain with the use of the teaching provided herein, which molecules and procedures will be useful for delivery of the therapeutic reagent to specific tissues.

It is to be understood that while the invention has been described in conjunction with the detailed description thereof, that the foregoing description is intended to illustrate and not limit the scope of the invention, which is defined by the scope of the appended claims. Other aspects, advantages, and modifications are within the scope of the following claims.

What is claimed is:

1. An isolated DNA molecule encoding a human herpes virus-8 (HHV-8) polypetide wherein said polypeptide is a membrane polypeptide expressed in an HHV-8 latently infected cell.

2. The DNA molecule of claim 1 consisting of DNA of SEQ ID NO:1.

3. A DNA molecule of claim 1 encoding the amino acid sequence set forth in SEQ ID NO. 2.

4. A substantially pure human herpes virus-8 (HHV-8) polypeptide comprising an amino acid sequence set forth in SEQ ID NO: 2.

5. An antibody that binds specifically to the human herpes virus-8 (HHV-8) membrane polypeptide encoded by the DNA of claim 1.

6. A method of detecting the presence of an immunogenic human herpes virus-8 (HHV-8) polypeptide in a patient, said method comprising:

a) contacting the antibody of claim 5 with a biological sample from said patient; and b) detecting binding of said HHV-8 polypeptide to said antibody.

7. An assay device comprising a solid support surface to which is attached a latently expressed HHV-8 membrane polypeptide.

8. The assay device of claim 7, wherein said polypeptide is encoded by SEQ ID NO:2.

9. An assay device comprising a solid support surface to which is attached an antibody that binds specifically to a latently expressed human herpes virus-8 (HHV-8) membrane polypeptide.

10. The assay device of claim 9 in which said membrane polypeptide comprises the amino acid sequence set forth in SEQ ID NO. 2.

11. An isolated DNA molecule encoding human herpes virus-8 (HHV-8) RNA transcript localized to the nucleus of an HHV-8 latently infected cell.

12. The DNA molecule of claim 11 consisting of DNA of SEQ ID NO:3.

* * * * *